US010253369B2

(12) United States Patent
Schnabel et al.

(10) Patent No.: US 10,253,369 B2
(45) Date of Patent: Apr. 9, 2019

(54) PREDICTING LIKELIHOOD OF RESPONSE TO COMBINATION THERAPY

(71) Applicant: BIOTHERANOSTICS, INC, San Diego, CA (US)

(72) Inventors: Catherine Schnabel, La Jolla, CA (US); Yi Zhang, San Diego, CA (US); Mark G. Erlander, Carlsbad, CA (US)

(73) Assignee: BIOTHERANOSTICS, INC., San Diego, CA (US)

( * ) Notice: Subject to any disclaimer, the term of this patent is extended or adjusted under 35 U.S.C. 154(b) by 604 days.

(21) Appl. No.: 14/724,732

(22) Filed: May 28, 2015

(65) Prior Publication Data

US 2015/0344967 A1 Dec. 3, 2015

Related U.S. Application Data

(60) Provisional application No. 62/004,471, filed on May 29, 2014.

(51) Int. Cl.
C12Q 1/68 (2018.01)
C12Q 1/6886 (2018.01)

(52) U.S. Cl.
CPC ..... C12Q 1/6886 (2013.01); C12Q 2600/106 (2013.01); C12Q 2600/158 (2013.01)

(58) Field of Classification Search
None
See application file for complete search history.

(56) References Cited

U.S. PATENT DOCUMENTS

| 6,291,170 B1 | 9/2001 | Van Gelder et al. |
| 6,794,141 B2 | 9/2004 | Erlander et al. |
| 2008/0085874 A1* | 4/2008 | Kushner ............ A61K 31/135 514/177 |
| 2011/0136680 A1 | 6/2011 | Erlander et al. |
| 2013/0281502 A1 | 10/2013 | Sgroi et al. |

FOREIGN PATENT DOCUMENTS

| WO | 2006/004600 A1 | 1/2006 |
| WO | 2009108215 A1 | 9/2009 |

OTHER PUBLICATIONS

Shah et al. (Cancer Res, 2013, 73(17):5449-5458, eDAT of Jul. 5, 2013).*
Cheang et al. (Annu. Rev. Pathol. Mech. Dis. 2008, 3:67-97).*
Ma et al. (2006, Journal of Clinical Oncology, 24(28):4611-4619) (Year: 2006).*
Draghici et al., A systems biology approach for pathway level analysis, Genome Research, 2007, pp. 1537-1545, vol. 17.
Korkaya et al., Regulation of Mammary Stem/Progenitor Cells by PTEN/Akt/b-Catenin Signaling, PLoS Bioloigy, 2009, e1000121, vol. 7(6).

(Continued)

Primary Examiner — Stephanie K Mummert
(74) Attorney, Agent, or Firm — Jones Day; Wenhua Yu

(57) ABSTRACT

Provided are methods of determining whether a subject having ER+ breast cancer is expected to benefit from treatment with combination endocrine therapy and mTOR inhibitor therapy. Also provided are methods of treating a subject having ER+ breast cancer.

18 Claims, 3 Drawing Sheets

(56) References Cited

OTHER PUBLICATIONS

Ma et al., A two-gene expression ratio predicts clinical outcome in breast cancer patients treated with tamoxifen, Cancer Cell, 2004, pp. 607-616, vol. 5.

Ma et al., The HOXB13:IL17BR Expression Index Is a Prognostic Factor in Early-Stage Breast Cancer, Journal of Clinical Oncology, 2006, 4611-4619, vol. 24.

Sgroi et al., Prediction of Late Disease Recurrence and Extended Adjuvant Letrozole Benefit by the HOXB13/IL17BR Biomarker, JNCI 2013, 1036-1042, vol. 105.

Shah et al., HOXB13 Mediates Tamoxifen Resistance and Invasiveness in Human Breast Cancer by Suppressing ERa and Inducing IL-6 Expression, Cancer Research, 2013, 5449-5458, vol. 73.

Tarca et al., A novel signaling pathway impact analysis, Bioinformatics, 2009, 75-82, vol. 25.

Turner et al., Adjuvant Chemotherapy: Which Patient? What Regimen?, ASCO University, 2013 Educational Book [Retrieved on Aug. 17, 2015). Online ebook. Retrieved from the Internet: <URL: http://meetinglibrary.asco.org/contenU145-132>; p. 5, first column, third paragraph.

* cited by examiner

PREDICTING LIKELIHOOD OF RESPONSE TO COMBINATION THERAPY

CROSS-REFERENCE TO RELATED APPLICATIONS

This application claims the benefit of U.S. Provisional Application No. 62/004,471, filed May 29, 2014, and incorporated by reference herein in its entirety.

BACKGROUND OF THE INVENTION (1) Field of the Invention

The present application generally relates to the identification and use of gene expression profiles with clinical relevance to breast cancer. In particular, the application relates to ER+ breast cancer and the use of HoxB13 gene expression to evaluate the likely responsiveness of the cancer to treatment options.

(2) Description of the Related Art

Elevated expression of HoxB13 is a predictor for patient benefit of extended adjuvant endocrine therapy in estrogen receptor-positive (ER+) breast cancer (U.S. Patent Application Publication 2013/0281502). As such, ER+ breast tumors that have elevated HoxB13 are associated with permissiveness to responsiveness to extended endocrine therapy such as with a selective estrogen receptor modulator (SERM) (e.g., tamoxifen), a selective estrogen receptor down-regulator (SERD) (e.g., fulvestrant), or an aromatase inhibitor (AI) (e.g., letrozole). However, the signaling pathways yielding this permissiveness to endocrine therapy responsiveness within ER+ breast cancer tumors containing elevated HoxB13 expression are not known.

The most frequently altered intracellular growth signaling pathway in breast cancer is PI3K/Akt/mTOR ("mTOR"), which is implicated as a key driver of proliferation and survival, particularly in ER+ tumors.

The mTOR signaling pathway (FIG. 1) and the ER pathway are implicated in bidirectional crosstalk, in which intracellular signaling pathways stimulate ER signaling through phosphorylation and activation of the receptor and its cofactors. In addition, estrogen stimulation of breast cancer cells immediately up-regulates intracellular kinase signaling, indicating that signaling through cytoplasmic or membrane bound estrogen receptors is involved in activation of mTOR signaling.

Central to the mTOR pathway is mTOR Complex 1 (mTORC1), a protein complex that acts as a nutrient/energy/redox sensor and regulates cell growth, proliferation and metabolism through translational control of essential proteins. Important substrates of mTORC1 are the 4E-binding protein 1 (4EBP1) and the p70 ribosomal S6 kinases 1 and 2 (S6K1 and S6K2), which are involved in regulation of the translational machinery. S6K1 amplification and S6K1 protein overexpression are associated with a poor outcome in breast cancer.

Phosphorylation of 4EBP1 by mTORC1 dissociates 4EBP1 from EIF4E, enabling EIF4E to induce protein translation. Phosphorylated 4EBP1 (p4EBP1) is thus a marker of activated mTOR signaling, and high levels of p4EBP1 in tumors have been associated with a worse outcome in several malignancies, whereas non-phosphorylated 4EBP1 has been considered a tumor suppressor. High levels of S6K2 and/or 4EBP1 have also been associated with a poor breast cancer prognosis. Furthermore, high cytoplasmic levels of 4EBP1 protein appears to predict a poor prognosis, and has been associated with a decreased benefit from endocrine treatment.

The mTOR pathway can be activated by the protein Akt when Akt is phosphorylated by a phosphoinositide 3-kinase (PI3 kinase). A mutation of Akt or PI3 kinase can activate those proteins, which can activate the mTOR pathway. Inhibitors of mTOR, Akt or PI3-kinase are available or are in clinical development to treat cancers caused by those mutations.

There is a need to understand the pathways involved in establishing and maintaining the permissive state in ER+ breast cancer. The present invention addresses that need.

BRIEF SUMMARY OF THE INVENTION

The present invention is based on the discovery that expression of HoxB13 is correlated with suppression of the mTOR pathway in ER+ breast cancer cells. Because high HoxB13 expression of ER+ breast cancer cells is also correlated with patient responsiveness to anti-estrogen therapy (i.e., endocrine therapy), an ER+ breast cancer tumor with high HoxB13 expression indicates that the patient is likely to respond to endocrine therapy in a cellular environment in which the mTOR pathway is suppressed. Therefore, patients with ER+ tumors containing high expression of HoxB13 have the likelihood to responding to a combination of an endocrine and an anti-mTOR pathway therapy.

In some embodiments, a method is provided for determining whether a subject having ER+ breast cancer is expected to benefit from treatment with combination endocrine therapy and mTOR inhibitor therapy. The method comprises:

(a) determining the expression level of the HoxB13 gene in a tissue or blood sample from the subject by preparing cDNA from HoxB13 mRNA extracted from the sample and quantifying the cDNA;

(b) comparing the expression level with reference expression levels of the HoxB13 gene in ER+ cells from reference breast cancer tumor cells that are (i) known to have high expression levels of the HoxB13 gene and/or (ii) known to have low expression levels of the HoxB13 gene;

(c) classifying the tumor cells from the subject as having high expression levels, or low expression levels, of HoxB13 based on the comparison in step (b); and (d) classifying the subject as likely to benefit from a combination endocrine therapy and mTOR inhibitor therapy if the subject has high HoxB13 and unlikely to benefit from the combination therapy if the subject has low HoxB13.

Also provided is a method of treating a subject having ER+ breast cancer. The method comprises:

(a) determining the expression level of the HoxB13 gene in a tissue or blood sample from the subject by preparing cDNA from HoxB13 mRNA extracted from the sample and quantifying the cDNA;

(b) comparing the expression level with reference expression levels of the HoxB13 gene in ER+ cells from reference breast cancer tumor cells that are (i) known to have high expression levels of the HoxB13 gene and/or (ii) known to have low expression levels of the HoxB13 gene;

(c) classifying the tumor cells from the subject as having high expression levels, or low expression levels, of HoxB13 based on the comparison in step (b); and (d) treating the subject with combination endocrine therapy and mTOR inhibitor therapy if the subject has high HoxB13 and not treating the subject with combination endocrine therapy and mTOR inhibitor therapy if the subject has low HoxB13.

DETAILED DESCRIPTION OF THE INVENTION

Figure 1:
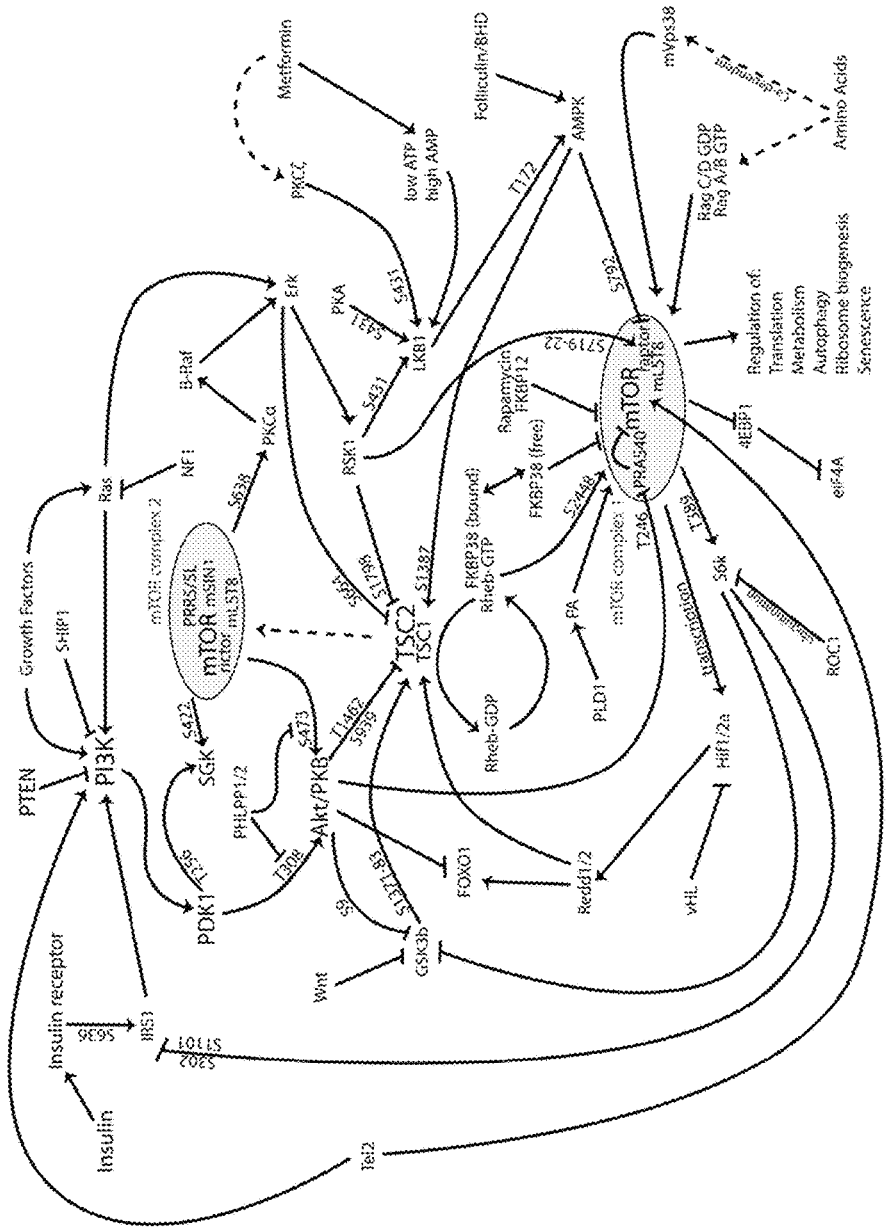
FIG. 1 is a graphic depiction of the mTOR signaling pathway.

As used herein, the singular forms "a", "an" and "the" are intended to include the plural forms as well, unless the context clearly indicates otherwise. Additionally, the use of "or" is intended to include "and/or", unless the context clearly indicates otherwise.

A gene expression "pattern" or "profile" or "signature" refers to the relative expression of one or more genes between two or more clinical outcomes, cancer outcomes, cancer recurrence and/or survival outcomes which is correlated with being able to distinguish between said outcomes. In some cases, the outcome is that of breast cancer.

A "gene", such as HoxB13, is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

The terms "correlate" or "correlation" or equivalents thereof refer to an association between expression of one or more genes, such as HoxB13, and a physiologic state of a cell to the exclusion of one or more other state as identified by use of the methods as described herein. A gene may be expressed at a higher or a lower level and still be correlated with one or more cancer state or outcome.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product that can be made enzymatically with DNA or RNA polymerases. "Amplification," as used herein, generally refers to the process of producing multiple copies of a desired sequence, particularly those of a sample. "Multiple copies" mean at least two copies. A "copy" does not necessarily mean perfect sequence complementarity or identity to the template sequence.

By "corresponding" is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al., 1990 (using the published default setting, i.e. parameters w=4, t=17). Methods for amplifying mRNA are generally known in the art, and include reverse transcription PCR (RT-PCR) and those described in U.S. Pat. No. 6,794,141. Another method which may be used is quantitative PCR (or Q-PCR). Alternatively, RNA may be directly labeled as the corresponding cDNA by methods known in the art.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about $50/cm^2$, more preferably at least about $100/cm^2$, even more preferably at least about $500/cm^2$, but preferably below about $1,000/cm^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Because the disclosure relies upon the identification of genes that are over- or under-expressed, one embodiment of the disclosure involves determining expression by hybridization of mRNA, or an amplified or cloned version thereof, of a sample cell to a polynucleotide that is unique to a particular gene sequence. Preferred polynucleotides of this type contain at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, or at least or about 400 basepairs of a gene sequence that is not found in other gene sequences. The term "about" as used in the preceding sentence refers to an increase or decrease of 10% from the stated numerical value. Such polynucleotides may also be referred to as polynucleotide probes that are capable of hybridizing to sequences of the genes, or unique portions thereof, described herein. Preferably, the sequences are those of mRNA encoded by the genes, the corresponding cDNA to such mRNAs, and/or amplified versions of such sequences. In preferred embodiments of the disclosure, the polynucleotide probes are immobilized on an array, other devices, or in individual spots that localize the probes.

In another embodiment of the disclosure, all or part of a disclosed sequence may be amplified and detected by methods such as the polymerase chain reaction (PCR) and variations thereof, such as, but not limited to, quantitative PCR (Q-PCR), reverse transcription PCR (RT-PCR), and real-time PCR, optionally real-time RT-PCR. Such methods would utilize one or two primers that are complementary to portions of a disclosed sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing sequences) of the disclosure under conditions which allow for their hybridization.

Alternatively, and in another embodiment of the disclosure, gene expression may be determined by analysis of expressed protein in a cell sample of interest by use of one or more antibodies specific for one or more epitopes of individual gene products (proteins) in said cell sample. Such antibodies are preferably labeled to permit their easy detection after binding to the gene product.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "cancer tissue sample" or "cancer cell sample" refers to a cell containing sample of tissue isolated from an individual afflicted with the corresponding cancer. The sample may be from material removed via a surgical procedure, such as a biopsy. Such samples are primary isolates (in contrast to cultured cells) and may be collected by any suitable means recognized in the art. In some embodiments, the "sample" may be collected by an non-invasive method, including, but not limited to, abrasion, fine needle aspiration.

A "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material. Of course the term may also be limited, if so indicated, as referring only to the transcription of nucleic acids.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present disclosure is based on the relative level of gene expression, mutations in non-coding regions of genes as disclosed herein may also be assayed in the practice of the disclosure.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Increases and decreases in expression of the disclosed sequences are defined in the following terms based upon percent or fold changes over expression in normal cells or other cells as defined. Increases may be of 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or fold over expression levels in normal cells. Decreases may be of 10, 20, 30, 40, 50, 55, 60, 65, 70, 75, 80, 82, 84, 86, 88, 90, 92, 94, 96, 98, 99 or 100% relative to expression levels in normal cells.

Unless defined otherwise all technical and scientific terms used herein have the same meaning as commonly understood to one of ordinary skill in the art to which this disclosure belongs.

The present invention is based in part on the discovery (described in the Example below) that high HoxB13 expression in ER+ breast cancer is correlated with an inhibited mTOR pathway in those cancers. Since high HoxB13 expression is also correlated with responsiveness to endocrine therapy, this discovery establishes a link between an inhibited mTOR pathway and responsiveness to endocrine therapy. As such, subjects having ER+ breast cancer that have high HoxB13 expression would be expected to benefit from a combination endocrine therapy and mTOR inhibitor therapy. Without being bound to any particular mechanism, it is believed that the mTOR inhibitor therapy in this combination serves to maintain permissiveness of the cancer to endocrine therapy by keeping the mTOR pathway inhibited.

Thus, in some embodiments, a method is provided for determining whether a subject having ER+ breast cancer is expected to benefit from treatment with combination endocrine therapy and mTOR inhibitor therapy. The method comprises:

(a) determining the expression level of the HoxB13 gene in a tissue or blood sample from the subject by preparing cDNA from HoxB13 mRNA extracted from the sample and quantifying the cDNA;

(b) comparing the expression level with reference expression levels of the HoxB13 gene in ER+ cells from reference breast cancer tumor cells that are (i) known to have high expression levels of the HoxB13 gene and/or (ii) known to have low expression levels of the HoxB13 gene;

(c) classifying the tumor cells from the subject as having high expression levels, or low expression levels, of HoxB13 based on the comparison in step (b); and (d) classifying the subject as likely to benefit from a combination endocrine therapy and mTOR inhibitor therapy if the subject has high HoxB13 and unlikely to benefit from the combination therapy if the subject has low HoxB13.

The HoxB13 expression patterns disclosed herein are predictive factors for therapeutic benefit for a combination therapy of anti-endocrine and anti-mTOR pathway therapy.

In some cases, the prediction is in node-negative breast cancer patients, such as ER+ node-negative patients as a non-limiting example.

To determine the expression levels of genes in the practice of the present disclosure, any method known in the art may be utilized. In some embodiments, expression based on detection of mRNA which hybridizes to the genes identified and disclosed herein is used. This is readily performed by any mRNA detection or amplification+detection method known or recognized as equivalent in the art such as, but not limited to, reverse transcription-PCR, the methods disclosed in U.S. Pat. No. 6,794,141, and methods to detect the presence, or absence, of mRNA stabilizing or destabilizing sequences.

Alternatively, expression based on detection of DNA status may be used. Detection of the DNA of an identified gene as methylated or deleted may be used for genes that have decreased expression. This may be readily performed by PCR based methods known in the art, including, but not limited to, Q-PCR. Conversely, detection of the DNA of an identified gene as amplified may be used for genes that have increased expression in correlation with a particular breast cancer outcome. This may be readily performed by PCR based, fluorescent in situ hybridization (FISH) and chromosome in situ hybridization (CISH) methods known in the art.

Expression based on detection of a presence, increase, or decrease in protein levels or activity may also be used. Detection may be performed by any immunohistochemistry (IHC)-based, blood-based (especially for secreted proteins), antibody (including autoantibodies against the protein)-based, exfoliate cell (from the cancer)-based, mass spectroscopy-based, or image (including used of labeled ligand)-based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

One embodiment using a nucleic acid based assay to determine expression is by immobilization of one or more sequences of the genes identified herein on a solid support, including, but not limited to, a solid substrate as an array or to beads or bead based technology as known in the art. Alternatively, solution based expression assays known in the art may be used.

The immobilized gene(s) may be in the form of polynucleotides that are unique or otherwise specific to the gene(s) such that the polynucleotide would be capable of hybridizing to a DNA or mRNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or mRNA corresponding to the gene(s) is not affected. In some cases, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

The immobilized gene(s) may be used to determine the state of nucleic acid samples prepared from sample cancer, or breast, cell(s) for which the outcome of the sample's subject (e.g. patient from whom the sample is obtained) is not known or for confirmation of an outcome that is already assigned to the sample's subject. Without limiting the disclosure, such a cell may be from a patient with ER+ breast cancer. The immobilized polynucleotide(s) need only be sufficient to specifically hybridize to the corresponding nucleic acid molecules derived from the sample under suitable conditions.

As will be appreciated by those skilled in the art, some of the corresponding sequences noted above, for example HoxB13, include 3' poly(A) (or poly(T) on the complementary strand) stretches that do not contribute to the uniqueness of the disclosed sequences. The disclosure may thus be practiced with sequences lacking the 3' poly(A) (or poly(T)) stretches. The uniqueness of the disclosed sequences refers to the portions or entireties of the sequences which are found only in the disclosed gene's nucleic acids, including unique sequences found at the 3' untranslated portion of the genes. Preferred unique sequences for the practice of the disclosure are those which contribute to the consensus sequences for each of the three sets such that the unique sequences will be useful in detecting expression in a variety of individuals rather than being specific for a polymorphism present in some individuals. Alternatively, sequences unique to an individual or a subpopulation may be used. The preferred unique sequences are preferably of the lengths of polynucleotides of the disclosure as discussed herein.

To determine the (increased or decreased) expression levels of the above described sequences in the practice of the disclosure, any method known in the art may be utilized. In one embodiment of the disclosure, expression based on detection of RNA which hybridizes to polynucleotides containing the above described sequences is used. This is readily performed by any RNA detection or amplification+detection method known or recognized as equivalent in the art such as, but not limited to, reverse transcription-PCR (optionally real-time PCR), the methods disclosed in U.S. Pat. Nos. 6,794,141 and 6,291,170, and quantitative PCR. Methods to identify increased RNA stability (resulting in an observation of increased expression) or decreased RNA stability (resulting in an observation of decreased expression) may also be used. These methods include the detection of sequences that increase or decrease the stability of mRNAs containing the genes' sequences. These methods also include the detection of increased mRNA degradation.

In some embodiments, including but not limited to use of tumor-enriched tissue lysates, for example enriched via microdissection, RNA is purified and subsequently reversed transcribed to generate cDNA. Because the starting tissue amounts from these samples are often limited, a multiplex pre-amplification ("preamp") step can be applied to the cDNA pool, for example using HoxB13 gene-specific primers. After the pre-amplification, the cDNA is then further processed, for example diluted and distributed into single-plex TaqMan PCR assays. This preamp step is useful to boost the representation of very low copy cDNAs that might not otherwise be discernible without pre-amplification. Any number of cycles of pre-amplification may be utilized, e.g., 2, 3, 4, 5, 6, 7, 8, 9, 10 or more.

Adding more cycles may not obviate the need to pre-amplify because the resolution afforded by conventional assays, for example TaqMan PCR, may not be very good between 1-10 copies (around PCR threshold cycles in the mid-to-upper 30s).

In some embodiments of the disclosure, polynucleotides having sequences present in the 3' untranslated and/or non-coding regions of the above disclosed sequences are used to detect expression levels of the gene sequences in cancer, or breast, cells. Such polynucleotides may optionally contain sequences found in the 3' portions of the coding regions of the above disclosed sequences. Polynucleotides containing a combination of sequences from the coding and 3' non-coding regions preferably have the sequences arranged contiguously, with no intervening heterologous sequences.

Alternatively, the disclosure may be practiced with polynucleotides having sequences present in the 5' untranslated and/or non-coding regions of the gene sequences in cancer, or breast, cells to detect their levels of expression. Such polynucleotides may optionally contain sequences found in the 5' portions of the coding regions. Polynucleotides containing a combination of sequences from the coding and 5' non-coding regions preferably have the sequences arranged contiguously, with no intervening heterologous sequences. The disclosure may also be practiced with sequences present in the coding regions of the disclosed gene sequences.

Non-limiting polynucleotides contain sequences from 3' or 5' untranslated and/or non-coding regions of at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Even more preferred are polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of the above described coding regions as found in polynucleotides of the disclosure are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

Polynucleotides combining the sequences from a 3' untranslated and/or non-coding region and the associated 3' end of the coding region may be at least or about 100, at least or about 150, at least or about 200, at least or about 250, at least or about 300, at least or about 350, or at least or about 400 consecutive nucleotides. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

In another embodiment of the disclosure, polynucleotides containing deletions of nucleotides from the 5' and/or 3' end of the above disclosed sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the disclosed sequences and the need to be able to use the polynucleotides for the detection of expression levels.

Other polynucleotides of the disclosure from the 3' end of the above disclosed sequences include those of primers and optional probes for quantitative PCR. In some embodiments, the primers and probes are those which amplify a region less than about 350, less than about 300, less than about 250, less than about 200, less than about 150, less than about 100, or less than about 50 nucleotides from the from the polyadenylation signal or polyadenylation site of a gene or expressed sequence.

In yet other embodiments of the disclosure, polynucleotides containing portions of the above disclosed sequences including the 3' end may be used. Such polynucleotides would contain at least or about 50, at least or about 100, at least about or 150, at least or about 200, at least or about 250, at least or about 300, at least or about 350, or at least or about 400 consecutive nucleotides from the 3' end of the disclosed sequences.

The disclosure also includes polynucleotides used to detect gene expression in breast cells. The polynucleotides may comprise a shorter polynucleotide consisting of sequences found in the above genes in combination with heterologous sequences not naturally found in combination with the sequences. Non-limiting examples include short sequences from cloning vectors or present in restriction fragments used to prepare labeled probes or primers as described herein.

The requisite level of expression may be that which is identified by the methods described herein for the genes used. Additionally, the assaying may include preparing mRNA from the sample, optionally for use in PCR (polymerase chain reaction) or other analytical methodology as described herein. The PCR methodology is optionally RT-PCR (reverse transcription-PCR) or quantitative PCR, such as real-time RT-PCR. Alternatively, the assaying may be conducted by use of an array, such as a microarray as known in the relevant field.

Any sample that can provide sufficient tumor mRNA to accurately measure HoxB13 expression levels therein can be utilized in these methods. In some embodiments, a blood sample is the source of the tumor mRNA, either as cell free tumor mRNA, e.g., in serum or plasma, or from circulating tumor cells, as is known in the art.

In other embodiments, the sample comprises ER+ tumor cells taken from the tumor in the breast of the subject. The nature of the cell containing sample is not limiting, as fresh tissue, freshly frozen tissue, and fixed tissue, such as formalin-fixed paraffin-embedded (FFPE) tissues, may be used in the disclosed methods. Such a sample can be collected by any method known in the art, including but not limited to a ductal lavage or fine needle aspirate sample. In some embodiments, the sample tumor cells are microdissected to isolate one or more cells suspected of being breast cancer cells.

The methods described herein can utilize breast cancer tumor cells from any type of ER+ breast cancer. In some embodiments, the breast cancer tumor cells from the subject are from a primary tumor. In other embodiments, the breast cancer tumor cells from the subject are from a metastatic tumor.

These methods can also utilize breast cancer tumor cells regardless of the mutational status of the cancer. In some embodiments, the tumor cells have a mutation that activates the mTOR pathway, e.g., in PI3K, Akt, or mTOR.

The ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene in the "transcriptome" (the transcribed fraction of genes in a genome) or the "proteome" (the translated fraction of expressed genes in a genome). Identifying features include, but are not limited to, unique nucleic acid sequences used to encode DNA or express RNA, said gene or epitopes specific to, or activities of, a protein encoded by said gene. All that is required is the identity of the gene(s) necessary to discriminate between cancer outcomes and an appropriate cell containing sample for use in an expression assay.

In one embodiment, the disclosure provides for the identification of the gene expression patterns by analyzing HoxB13 gene expression from single cells or homogenous cell populations which have been dissected away from, or otherwise isolated or purified from, contaminating cells beyond that possible by a simple biopsy. Because the expression of numerous genes fluctuate between cells from different patients as well as between cells from the same patient sample, the levels of gene expression may be determined in correspondence to one or more "control" or "normalization" genes, the expression(s) of which are relatively constant in the cells of a patient or between patients. A nonlimiting example of a good control gene for these methods is HoxC13, which is an ortholog of, and functionally related to, HoxB13.

One advantage provided by obtaining a homogeneous cell population is that contaminating, non-cancer cells (such as infiltrating lymphocytes or other immune system cells) are not present to possibly affect the genes identified or the subsequent analysis of gene expression to identify the cancer recurrence and/or survival outcomes of patients. Such contamination is present where a biopsy containing many cell types is used to assay gene expression profiles.

A cutoff value using HoxB13 expression may be used to define breast cancer cells as having either a "high HoxB13" or a "low HoxB13" value. The invention is not narrowly limited to any particular method of determining the cutoff value. For any of the above-described methods of determining HoxB13 expression levels, the skilled artisan could determine a proper cutoff value without undue experimentation. As a non-limiting example, the value of 0.06 may be used in the manner of Ma et al., 2006. In other embodiments, the cutoff is the average expression of HoxB13 in breast cancer cells from afflicted subjects. In alternative embodiments, the cutoff is determined using appropriate statistical analysis to determine the anti-mode in the bimodal distribution of HoxB13. The cutoff value can also be set by setting the sensitivity of the assay for expression such that the low HoxB13 is measured as undetectable.

While the present disclosure is described mainly in the context of human cancer, such as breast cancer, it may be practiced in the context of cancer of any animal. Preferred animals for the application of the present disclosure are mammals, particularly those important to agricultural applications (such as, but not limited to, cattle, sheep, horses, and other "farm animals"), animal models of cancer, and animals for human companionship (such as, but not limited to, dogs and cats).

The methods provided by the disclosure may also be automated in whole or in part.

The materials for use in the methods of the present disclosure are ideally suited for preparation of kits produced in accordance with well-known procedures. The disclosure thus provides kits comprising agents for the detection of expression of the disclosed genes for grading tumors or determining cancer outcomes. Such kits optionally comprise the agent with an identifying description or label or instructions relating to their use in the methods of the present disclosure. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present disclosure (e.g., appropriate length poly(T) or random primers linked to a promoter reactive with the RNA polymerase). A set of instructions will also typically be included.

In some embodiments the above-described methods also comprise recommending combination endocrine therapy and mTOR inhibitor therapy for the subject if the subject has high HoxB13 and not recommending combination endocrine therapy and mTOR inhibitor therapy for the subject if the subject has low HoxB13. The recommendation can be made to the patient, the doctor, the caregiver, the patient records or any other relevant receiver. Additionally, the recommendation can be made orally or in writing, e.g., as in a test report to the doctor or the patient.

In various embodiments of any of the above methods, the subject is treated with combination endocrine therapy and mTOR inhibitor therapy if the subject has high HoxB13 and not treated with combination endocrine therapy and mTOR inhibitor therapy if the subject has low HoxB13.

The above methods may be performed at any time after breast cancer diagnosis. In some embodiments, the methods are performed around the time of diagnosis (e.g., within a week, two weeks, three weeks, a month, or two, three, four, five or six months after diagnosis).

In other embodiments, the methods are performed after the subject has undergone initial endocrine therapy for at least one, two, three, four or five years and an FFPE sample was taken before the initial endocrine therapy commenced. Under those circumstances, the subject is classified as likely to benefit from a combination extended endocrine therapy and mTOR inhibitor therapy if the subject has high HoxB13 and unlikely to benefit from the combination extended therapy if the subject has low HoxB13. Those methods can further comprise recommending combination extended endocrine therapy and mTOR inhibitor therapy for the subject if the subject has high HoxB13 and not recommending combination extended endocrine therapy and mTOR inhibitor therapy for the subject if the subject has low HoxB13. Those methods can also further comprise treating the subject with combination extended endocrine therapy and mTOR inhibitor therapy if the subject has high HoxB13 and not treating the subject with combination extended endocrine therapy and mTOR inhibitor therapy if the subject has low HoxB13.

Where the subject is treated subsequent to testing, the treatment is not narrowly limited to the use of any specific endocrine or mTOR inhibitors. In some embodiments, the endocrine therapy comprises treatment with a selective estrogen receptor modulator (SERM), a selective estrogen receptor down-regulator (SERD), and/or an aromatase inhibitor (AI). In various embodiments, the endocrine therapy comprises treatment with tamoxifen. In additional embodiments, the endocrine therapy comprises treatment with letrozole or anastrozole.

In some embodiments, the mTOR inhibitor therapy comprises treatment with a rapamycin analog, e.g., temsirolimus, everolimus, or ridaforolimus. In other embodiments, the mTOR inhibitor therapy comprises treatment with a PI3K inhibitor, e.g., wortmannin, demethoxyviridin, LY294002, perifosine, idelalisib, IC486068 or IC87114. In additional embodiments, the mTOR inhibitor therapy comprises treatment with an Akt inhibitor, e.g., perifosine.

As discussed in the Example below, high HoxB13 expression in ER+ breast cancer is correlated with an inhibited cell cycle pathway in those cancers. As such, molecular assays that measure cell cycle components, such as the molecular grade index (MGI) described in U.S. Patent Application Publication US 2011/0136680, can substitute, or be combined with the HoxB13 analysis utilized in the above-described methods, to determine whether the combination therapy is likely to benefit a subject with ER+ breast cancer.

Preferred embodiments are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example. Pathway Correlates in ER-positive Primary Breast Tumors with High HoxB13

Background

HOXB13 expression level predicts the benefit of extended adjuvant endocrine therapy in ER-positive (ER+) breast cancer (U.S. Patent Application Publication 2013/0281502). However, the underlying mechanistic basis of the difference between cancers that respond to extended therapy (correlated with high HoxB13 expression) and cancers that are resistant to extended therapy (correlated with low HoxB13 expression) remains poorly understood. In this study, in order to determine the pathways implicated in the permissiveness or resistance of ER+ breast cancer to endocrine therapy, exploratory pathway analyses were conducted comparing ER+ breast tumors with High- vs Low-HOXB13 expression using The Cancer Genome Atlas (TCGA) genomic dataset.

Pathway analysis methods using traditional statistical models (e.g. enrichment analysis by hypergeometric distribution) fail to take into consideration important biological interactions, thus providing incorrect results in certain situations. A technique that takes biological interactions into consideration is signaling pathway impact analysis (SPIA).

SPIA considers the information from a set of differentially expressed genes and their fold changes, as well as pathway topology (type, position, interaction) in order to assess the significance of the pathways in the condition under the study. It not only provides standard p value for gene enrichment (pNDE—Tables 2, 3, 4 and 6), but also provides a p value for evaluating pathway topology (pPERT) and a combined p value (pG) for evaluating the combined evidence. See Tarca et al., 2009 and Draghici et al., 2007.

Methods

Differential expression of mRNA (Agilent 244K array) and protein (MD Anderson reverse phase protein array) of ER+ breast tumors from the The Cancer Genome Atlas (TCGA) Data Portal were evaluated by t-tests based on bimodal HOXB13 expression (High vs Low). Network models with altered activity were evaluated using Signaling Pathway Impact Analysis (SPIA) that provides a p-value capturing both gene-set enrichment and perturbation on a given pathway based on topology. HOXC13 was used as a negative control. Findings were independently validated using the Netherland Cancer Institute (NKI 295) breast cancer dataset.

The SPIA analysis was executed using Bioconductor software (at the website bioconductor.org), on five pathway databases:

The Kyoto Encyclopedia of Genes and Genomes (KEGG) pathway database (at the website genome.jp/kegg/pathway.html);

The Reactome database (at the website reactome.org/);

BioCarta (incomplete annotation) (at the website biocarta.com/genes/index.asp);

The NCI Pathway Interaction Database (no update since September 2012) (at the website pid.nci.nih.gov/); and Signaling Pathway Integrated Knowledge Engine (SPIKE) (small, no update since January 2012) (at the website cs.tau.ac.il/~spike/).

The platforms and sample sizes for the various characteristics analyzed for HoxB13 expression are shown in Table 1. The SPIA analysis using RNA gene expression utilized 375 ER+ tumors, 239 HoxB13 high expressers, and 136 HoxB13 low expressers. 17142 unique genes with ENTREZ ID analyzed; 433 and 1331 genes were differentially expressed (DE) by t tests using a p value cutoff 0.001 & 0.01, respectively.

TABLE 1

Platforms and sample sizes.

| Genomic Technology | Platform | Feature | HOXB13 | ER+ N | ER+ H group | N0ER+ N | N0ER+ H group |
|---|---|---|---|---|---|---|---|
| Sequencing | Paired-end Sequencing on Illumina HiSeq2000 | NA | High | 362 | 129 | 175 | 56 |
| | | | Low | | 233 | | 119 |
| RNA expression | Agilent 244K | 17161 | High | 375 | 136 | 184 | 59 |
| | | | Low | | 239 | | 125 |
| Protein Expression | MDA Reverse Phase Protein Array | 165 | High | 280 | 104 | 133 | 44 |
| | | | Low | | 176 | | 89 |
| Methylation | Illumina Infinium HumanMethylation 27 & 450 | 23059 | High | 340 | 123 | 173 | 57 |
| | | | Low | | 217 | | 116 |

The gene HoxC13, a functionally related ortholog of HoxB13, was used as a control in the analysis. The expression of that gene showed no association with mTOR pathway gene expression.

Results

Figure 2:
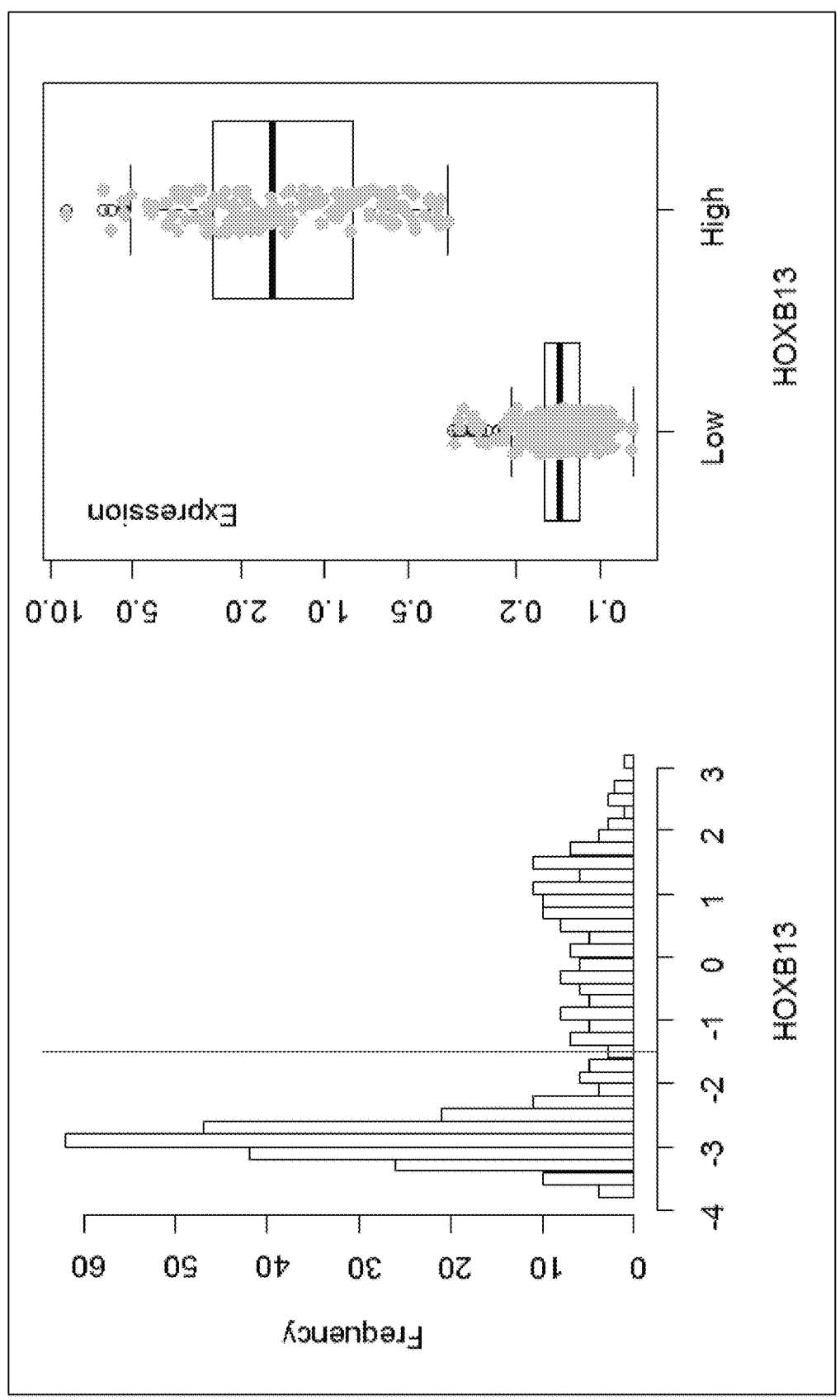
FIG. 2 is graphs showing that HoxB13 has bimodal distribution in breast tumors.

TCGA gene expression data from 375 ER+ breast tumors were included. HoxB13 expression showed a clear bimodal distribution (FIG. 2). Of 17142 unique genes analyzed, 1331 genes showed differential expression between high (N=239) and low (N=136) HOXB13 tumors (p<0.01). SPIA analyses of high HOXB13-expressing tumors using KEGG showed the top ranking pathway alterations were mTOR (p=0.015), cell cycle (p=0.026), and DNA repair (Fanconi anemia) (p=0.035) (Table 2).

TABLE 2

RNA expression using KEGG. In order of P value

| Name | pSize | NDE | pNDE | tA | pPERT | pG | Status |
|---|---|---|---|---|---|---|---|
| mTOR signaling pathway | 62 | 6 | 0.351 | −17.835652 | 0.006 | 0.015 | Inhibited |
| Cell cycle | 122 | 18 | 0.006 | −12.637336 | 0.633 | 0.026 | Inhibited |
| Fanconi anemia pathway | 47 | 8 | 0.027 | 7.615679 | 0.207 | 0.035 | Activated |
| ECM-receptor interaction | 84 | 4 | 0.900 | −14.926591 | 0.013 | 0.064 | Inhibited |
| Morphine addiction | 91 | 6 | 0.720 | 16.385839 | 0.021 | 0.078 | Activated |
| Tuberculosis | 170 | 4 | 0.999 | 39.006803 | 0.019 | 0.094 | Activated |
| Viral myocarditis | 67 | 2 | 0.971 | 14.341050 | 0.028 | 0.125 | Activated |
| Pathways in cancer | 322 | 27 | 0.369 | −84.812289 | 0.083 | 0.138 | Inhibited |
| Melanoma | 70 | 4 | 0.804 | −51.527098 | 0.042 | 0.148 | Inhibited |
| p53 signaling pathway | 67 | 9 | 0.074 | 6.741727 | 0.478 | 0.153 | Activated |
| Bacterial invasion of epithelial cells | 69 | 3 | 0.912 | −29.312449 | 0.067 | 0.232 | Inhibited |
| Neurotrophin signaling pathway | 119 | 5 | 0.959 | −30.705962 | 0.065 | 0.235 | Inhibited |
| Shigellosis | 61 | 3 | 0.863 | −16.596679 | 0.093 | 0.283 | Inhibited |
| Mineral absorption | 49 | 7 | 0.083 | 0.000000 | 1.000 | 0.290 | Inhibited |
| Influenza A | 163 | 5 | 0.996 | −14.490041 | 0.093 | 0.313 | Inhibited |

An SPIA analysis of RNA from the reactome database (Table 3) as well as protein expression analysis (Table 4) revealed a negative trend (i.e., high HoxB13 expression correlates with low mTOR pathway expression), consistent with the KEGG data, but the trend was not significant in either analysis.

TABLE 3

Inhibition of mTOR pathway supported by RNA analysis with reactome databases

| Name | pSize | NDE | pNDE | tA | pPERT | pG | Status |
|---|---|---|---|---|---|---|---|
| mTOR signaling | 26 | 1 | 0.878 | −11.30372 | 0.367 | 0.687 | Inhibited |

TABLE 4

Inhibition of mTOR signaling pathway supported by protein analysis using KEGG

| Name | pSize | NDE | pNDE | tA | pPERT | pG | Status |
|---|---|---|---|---|---|---|---|
| mTOR signaling pathway | 17 | 6 | 0.575 | −7.42516 | 0.067 | 0.164 | Inhibited |

Correlations of protein expression levels of HoxB13 with individual components of the mTOR pathway showed mixed trends (Table 5).

TABLE 5 mTOR protein expression between High- vs Low- HOXB13

| Gene | Expression | stat | P |
|---|---|---|---|
| EIF4EBP1 | protein | 1.738 | 0.083 |
| IRS1 | protein | −2.381 | 0.018 |
| MAPK1 | phosphorylation | −2.665 | 0.008 |
| RPS6 | phosphorylation | 1.799 | 0.073 |
| RPS6 | protein | 1.671 | 0.096 |
| RPS6KA1 | phosphorylation | −2.122 | 0.035 |
| RPS6KB1 | phosphorylation | 1.653 | 0.099 |

Figure 3:
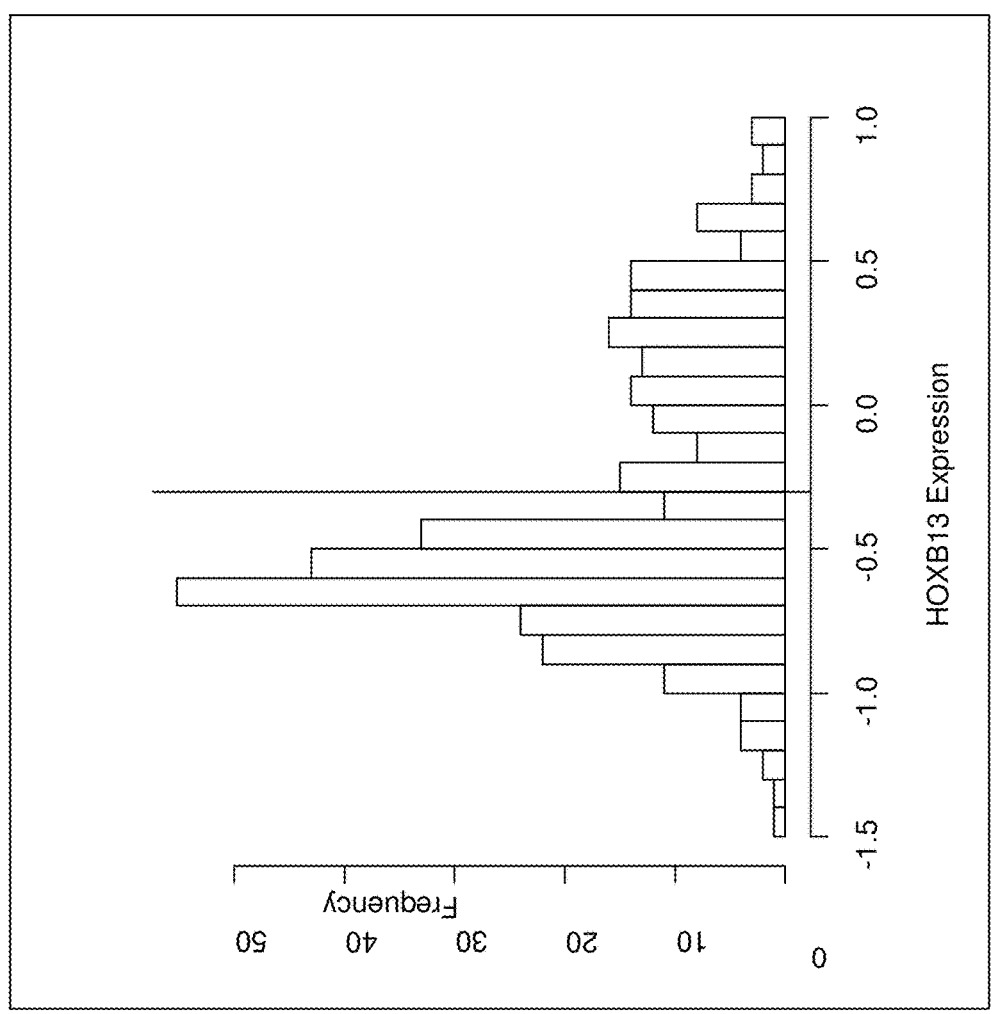
FIG. 3 is a graph showing the bimodal distribution of HoxB13 in the NKI dataset.

Independent analysis of 249 ER+ tumors from the NKI dataset also revealed a bimodal distribution of HoxB13 expression (FIG. 3). The SPIA analysis showed a consistent trend toward inhibition of the mTOR pathway in high HoxB13 tumors (Table 6).

TABLE 6

NKI dataset supports inhibition of mTOR signaling pathway

| Name | pSize | NDE | pNDE | tA | pPERT | pG | Status |
|---|---|---|---|---|---|---|---|
| mTOR signaling pathway | 58 | 5 | 0.535 | −2.77402 | 0.631 | 0.704 | Inhibited |

Although not significant, pathway analysis with NKI indicated an "Inhibited" status in the high HoxB13 tumors.

The suppression of the mTOR pathway was further evaluated through inspection of mTOR effector, 4EBP1. Both TCGA and NKI datasets showed a significantly higher gene expression of 4EBP1 (p=0.026 and 0.002, respectively) (Table 7). In addition, the TCGA data showed higher protein expression of 4EBP1 (p=0.083).

TABLE 7

EIF4EBP1 expression in TCGA and NKI datasets

| SYMBOL | ENTREZID | stat | p.values |
|---|---|---|---|
| A. TCGA Dataset | | | |
| 4EBP1 | 1978 | 2.23 | 0.026 |
| S6K1 | 6198 | 1.77 | 0.078 |
| S6K2 | 6199 | 5.25 | <0.0001 |
| B. NKI Dataset | | | |
| 4EBP1 | 1978 | 3.20 | 0.002 |
| S6K1 | 6198 | 2.35 | 0.019 |
| S6K2 | 6199 | 1.49 | 0.139 |

The consistent higher expression of the mTOR substrate 4EBP1 in both datasets supports the indication that the mTOR pathway is being inhibited in high HoxB13 tumors.

Discussion

This analysis revealed potential functional interaction between HoxB13 expression and the mTOR pathway, wherein high HoxB13 expression was associated with repressed mTOR signaling in these tumors. That relationship was revealed in the analysis with both KEGG and Reactome databases. Independent analysis using the NKI dataset confirmed the repression of the mTOR signaling pathway in high HoxB13-expressing tumors, with higher expression of 4EBP1 in high HoxB13-expressing tumors in both the TCGA and NKI datasets. Furthermore, protein expression analysis confirmed higher expression of 4EBP1 in high HoxB13 tumors.

REFERENCES

Altschul et al., J. Mol. Biol. 215:403-410 (1990)
Draghici et al., Genome Res. 17:1537-1545 (2007)
Ma et al., J. Clin. Oncol. 24:4611-9 (2006)
Tarca et al., Bioinformatics 25:75-82 (2009)
U.S. Pat. No. 6,291,170
U.S. Pat. No. 6,328,709
U.S. Pat. No. 6,794,141
U.S. Patent Application Publication US 2011/0136680
U.S. Patent Application Publication US 2013/0281502

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of determining whether a subject having ER+ breast cancer is expected to benefit from treatment with combination endocrine therapy and mTOR inhibitor therapy, the method comprising:
   (a) determining the expression level of the HoxB13 gene in a tissue or blood sample from the subject by preparing cDNA from HoxB13 mRNA extracted from the sample and quantifying the cDNA;
   (b) comparing the expression level with reference expression levels of the HoxB13 gene in ER+ cells from reference breast cancer tumor cells that are (i) known to have high expression levels of the HoxB13 gene and/or (ii) known to have low expression levels of the HoxB13 gene;
   (c) classifying the tumor cells from the subject as having high expression levels, or low expression levels, of HoxB13 based on the comparison in step (b);
   (d) classifying the subject as likely to benefit from a combination endocrine therapy and mTOR inhibitor therapy if the subject has high HoxB13 and unlikely to benefit from the combination therapy if the subject has low HoxB13; and
   (e) treating the subject with combination endocrine therapy and mTOR inhibitor therapy if the subject has high HoxB13 and not treating the subject with combination endocrine therapy and mTOR inhibitor therapy if the subject has low HoxB13.

2. A method of determining whether a subject having ER+ breast cancer is expected to benefit from treatment with combination endocrine therapy and mTOR inhibitor therapy, the method comprising:
   (a) determining the expression level of the HoxB13 gene in a tissue or blood sample from the subject by preparing cDNA from HoxB13 mRNA extracted from the sample and quantifying the cDNA;
   (b) comparing the expression level with reference expression levels of the HoxB13 gene in ER+ cells from reference breast cancer tumor cells that are (i) known to have high expression levels of the HoxB13 gene and/or (ii) known to have low expression levels of the HoxB13 gene;
   (c) classifying the tumor cells from the subject as having high expression levels, or low expression levels, of HoxB13 based on the comparison in step (b);
   (d) classifying the subject as likely to benefit from a combination endocrine therapy and mTOR inhibitor therapy if the subject has high HoxB13 and unlikely to benefit from the combination therapy if the subject has low HoxB13; and
   (e) recommending combination endocrine therapy and mTOR inhibitor therapy for the subject if the subject has high HoxB13 and not recommending combination endocrine therapy and mTOR inhibitor therapy for the subject if the subject has low HoxB13.

3. The method of claim 1, wherein the preparing and quantifying of step (a) is by quantitative reverse transcription PCR.

4. The method of claim 1, wherein the preparing and quantifying of step (a) comprises pre-amplification of the HoxB13 cDNA.

5. The method of claim 1, wherein serum or plasma isolated from a blood sample from the subject is utilized in the determining step.

6. The method of claim 1, wherein the expression level of the HoxB13 gene in circulating tumor cells or cell free mRNA is determined.

7. The method of claim 1, wherein the sample comprises ER+ breast cancer tumor cells from the breast of the subject.

8. The method of claim 7, wherein the sample tumor cells are from a ductal lavage or fine needle aspirate sample, and/or the sample tumor cells are microdissected to isolate one or more cells suspected of being breast cancer cells.

9. The method of claim 7, wherein the sample tumor cells are from a formalin fixed paraffin embedded (FFPE) sample.

10. The method of claim 9, wherein the subject has undergone initial endocrine therapy for at least four years and the FFPE sample was taken before the initial endocrine therapy commenced; and the subject is classified as likely to benefit from a combination extended endocrine therapy and mTOR inhibitor therapy if the subject has high HoxB13 and unlikely to benefit from the combination extended therapy if the subject has low HoxB13.

11. The method of claim 2, wherein the sample is a formalin fixed paraffin embedded (FFPE) sample comprising ER+ breast cancer tumor cells from of the breast of the subject, and wherein the subject has undergone initial endocrine therapy for at least four years and the FFPE sample was taken before the initial endocrine therapy commenced; and the subject is classified as likely to benefit from a combination extended endocrine therapy and mTOR inhibitor therapy if the subject has high HoxB13 and unlikely to benefit from the combination extended therapy if the subject has low HoxB13.

12. The method of claim 1, wherein the endocrine therapy comprises treatment with a selective estrogen receptor modulator (SERM), a selective estrogen receptor down-regulator (SERD), and/or an aromatase inhibitor (AI).

13. The method of claim 12, wherein the endocrine therapy comprises treatment with tamoxifen, letrozole or anastrozole.

14. The method of claim 1, wherein the mTOR inhibitor therapy comprises treatment with a rapamycin analog, a PI3K inhibitor or an Akt inhibitor.

15. The method of claim 14, wherein the mTOR inhibitor therapy comprises treatment with temsirolimus, everolimus, or ridaforolimus wortmannin, demethoxyviridin, LY294002, perifosine, idelalisib, IC486068, IC87114, or perifosine.

16. The method of claim 1, wherein the breast cancer tumor cells from the subject are from a primary tumor.

17. The method of claim 1, wherein the breast cancer tumor cells from the subject are from a metastatic tumor.

18. The method of claim 1, wherein the breast cancer tumor cells from the subject have a mutation that activates mTOR.

* * * * *